US006536940B1

(12) United States Patent
Kolb et al.

(10) Patent No.: US 6,536,940 B1
(45) Date of Patent: Mar. 25, 2003

(54) PREPARATION OF LIQUID DISPERSIONS

(75) Inventors: Gudrun Kolb, Bremen (DE); Hermann Stein, Liestal (CH); Klaus Viardot, Riehen (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 10/174,178

(22) Filed: Jun. 18, 2002

Related U.S. Application Data

(62) Division of application No. 09/455,135, filed on Dec. 6, 1999.

(30) Foreign Application Priority Data

Dec. 7, 1998 (EP) .......................................... 98123237

(51) Int. Cl.[7] .................................................. B01F 5/06

(52) U.S. Cl. .................... 366/336; 366/336; 366/176.1; 426/519

(58) Field of Search ............................ 366/176.1, 336, 366/340, 348; 138/42, 40; 426/519

(56) References Cited

U.S. PATENT DOCUMENTS

| | | | |
|---|---|---|---|
| 1,503,371 | A | 7/1924 | Meyer |
| 1,515,408 | A | 11/1924 | Puffer |
| 1,654,936 | A | 1/1928 | Jones |
| 1,788,660 | A | 1/1931 | Colomb |
| 2,125,245 | A | 7/1938 | McCray |
| 2,132,854 | A | 10/1938 | Knott |
| 2,198,614 | A | 4/1940 | Hayes |
| 2,929,248 | A | 3/1960 | Sprenkle |
| 2,965,695 | A | 12/1960 | Sleicher |
| 3,526,391 | A | 9/1970 | Church |
| 3,545,492 | A | 12/1970 | Scheid |
| 3,572,391 | A | 3/1971 | Hirsch |
| 3,582,048 | A | 6/1971 | Sarem |
| 3,665,965 | A | 5/1972 | Baumann |
| 3,725,186 | A | 4/1973 | Lynch |
| 3,780,946 | A | 12/1973 | Smith et al. |
| 3,899,001 | A | 8/1975 | Orme |
| 4,000,086 | A | 12/1976 | Stoev |
| 4,427,030 | A | 1/1984 | Jouwsma |
| 4,501,501 | A | 2/1985 | Edwards |
| 4,514,095 | A | 4/1985 | Ehrfeld |
| 4,529,561 | A | 7/1985 | Hunt et al. |

(List continued on next page.)

FOREIGN PATENT DOCUMENTS

| | | |
|---|---|---|
| CA | 2237554 | 11/1996 |
| DE | 39 05 354 A1 | 8/1990 |
| DE | 195 42 499 A1 | 5/1997 |
| EP | 0 766 997 A1 | 4/1997 |
| WO | WO 94/08626 | 4/1994 |
| WO | WO 97/17946 | 5/1997 |

OTHER PUBLICATIONS

Stang, et al., "Zerkleinern and Stabilisiern von Tropfen beim mechanischen Emulgieren," Fortscher.–Ber. VDI Reihe 3 Nr. 527 Düsseldorf: VDI Verlag 1998.

Patent Abstracts of Japan, Abstract of JP 63107736 (1988).

Derwent English language abstract of DE 3905354 (document B4).

*Primary Examiner*—Tony G. Soohoo
(74) *Attorney, Agent, or Firm*—Bryan Cave LLP

(57) ABSTRACT

A process for mixing or dispersing liquids is provided that includes introducing liquids to be mixed or dispersed into a mixing device having a cylindrical support. The cylindrical support includes an inlet nozzle having a bore which is in fluid communication through a turbulence chamber with a bore of an outlet nozzle, wherein the bores of the nozzles are axially spaced apart relative to one another. The liquids are then allowed to enter the turbulence chamber through the bore of the inlet nozzle where the liquids are mixed or dispersed. The mixed or dispersed liquid is then recovered from the outlet nozzle. Various devices for mixing or dispersing liquids are also provided.

14 Claims, 3 Drawing Sheets

4
5 6 7 8

U.S. PATENT DOCUMENTS 4,621,023 A 11/1986 Redziniak et al.
4,679,579 A 7/1987 Megee et al.
4,787,419 A 11/1988 Megee
5,326,484 A 7/1994 Nakashima et al.
5,327,941 A 7/1994 Bitsakis
5,547,281 A 8/1996 Brooks
5,672,821 A 9/1997 Suzuki
5,810,266 A 9/1998 Nyssen et al.
5,863,587 A 1/1999 Badertscher et al.
5,984,519 A 11/1999 Onodera
6,213,453 B1 4/2001 Ou
6,331,314 B1 * 12/2001 Klinksiek et al. ........... 424/450

* cited by examiner

PREPARATION OF LIQUID DISPERSIONS

This is a divisional of U.S. application Ser. No. 09/455,135, filed Dec. 6, 1999.

FIELD OF THE INVENTION

The present invention provides a process for mixing or dispersing liquids. In particular, a process for the production of a finely divided liquid dispersion is provided, as well as mixing devices for carrying out the process.

BACKGROUND OF THE INVENTION

European Patent Publication EP 0776 997 A1 describes a method for the production of a finely divided dispersion of solids in which a pre-dispersion is pumped through one or more slotted nozzles. The particle size of the dispersed phase lies in the region of 0.01 $\mu$m to 20 $\mu$m. The diameter of the nozzle bore is 0.05 mm to 1 mm. The ratio of bore length to bore diameter is 1:1 to 1:10. A preferred combination includes a device which has two nozzle bodies with the nozzles lying opposite their outlet. Also described are devices in which the crude dispersion or pre-dispersion is pumped through two or more nozzles having an equal or decreasing bore diameter. The slotted nozzle suitably consists of a ceramic material, for example, zirconium oxide, or a metal coated with ceramic.

International Patent Publication WO 97/17946 describes a method for the production of a liposome dispersion in which an aqueous pre-dispersion of one or more amphiphilic substances is pumped at 600 bar to 900 bar through at least one homogenizing nozzle having a diameter of 0.1 mm to 0.5 mm. The homogenizing nozzle has an inlet channel and an outlet channel and includes a hard ceramic plate, in which the bore is situated, pressed in a steel body. The inlet channel and the outlet channel are also incorporated in the steel body. When several nozzles are used, they are arranged opposite to each other and have a parallel inflow. The pre-dispersion is pumped in the circuit through the homogenizing nozzle until the average particle size of the liposome dispersion is between about 35 nm and about 80 nm.

SUMMARY OF THE INVENTION

The devices described above suffer from the drawback that intermixing is often inefficient or incomplete. Moreover, such devices require high amounts of energy to achieve viable levels of intermixing.

Accordingly, it would be desirable to provide a method for mixing or dispersing liquids which permits an improved intermixing with lower energy expenditure compared with the state of the art.

One embodiment of the invention is a process for mixing or dispersing liquids that includes introducing liquids to be mixed or dispersed into a mixing device having a cylindrical support. The cylindrical support includes an inlet nozzle having a bore which is in fluid communication through a turbulence chamber with a bore of an outlet nozzle, wherein the bores of the nozzles are axially spaced apart relative to one another. The liquids then enter the turbulence chamber through the bore of the inlet nozzle where the liquids are subjected to turbulence, i.e., are mixed or dispersed. The mixed or dispersed product is thereafter recovered from the outlet nozzle.

Another embodiment of the present invention is a mixing device having a cylindrical support. The cylindrical support includes an inlet nozzle having a bore which is in fluid communication through a turbulence chamber with a bore of an outlet nozzle, wherein the bores of the nozzles are axially spaced apart relative to one another.

Another embodiment of the invention is a scale up arrangement wherein a plurality of nozzles are disposed within the cylindrical support.

A further embodiment of the invention is a scale up arrangement that includes a first support disk, a turbulence chamber, and a second support disk, which are positioned in sequence in a conduit. The first support disk consists of a plurality of inlet nozzles having a bore diameter of about 0.05 mm to about 1 mm. The second support disk contains a plurality of outlet nozzles having a bore diameter of about 0.05 mm to about 1 mm. The bores of the inlet nozzles are in fluid communication with the bores of the outlet nozzles through the turbulence chamber and the bores of the inlet nozzles and outlet nozzles are axially spaced apart relative to one another.

DETAILED DESCRIPTION OF THE INVENTION

Figure 1:
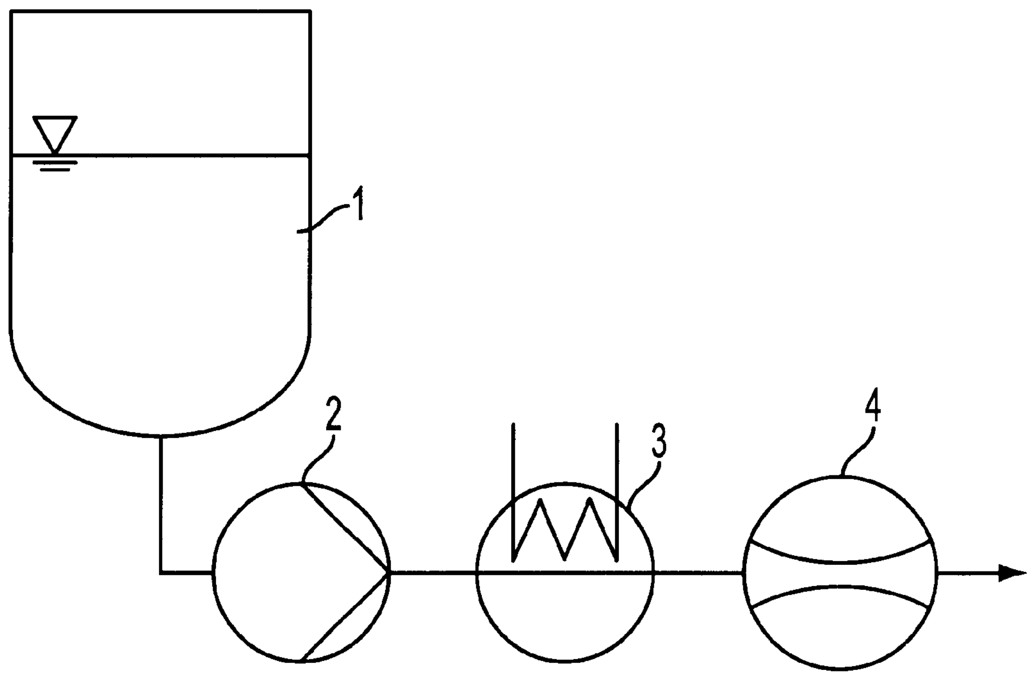
FIG. 1 shows a flow diagram for carrying out the process in accordance with the invention.

The present invention solves the problem of the previously described devices by pumping the liquids to be mixed or to be dispersed at temperatures of about 20° C. to about 250° C., preferably of about 20° C. to about 200° C., and pressures of about 50 bar to about 2500 bar, preferably of about 100 bar to about 800 bar, through a mixing device which consists of one or more inlet nozzles, one or more turbulence chambers and one or more outlet nozzles, with the inlet nozzle(s), turbulence chamber(s) and outlet nozzle(s) being pressed in sequence in a cylindrical support. The bores of the inlet nozzles are in fluid communication with the bores of the outlet nozzles through the turbulence chamber and the bores of the inlet and outlet nozzles are axially spaced apart relative to one another.

The process of the invention is especially suitable for the production of finely divided dispersions having average particle sizes of about 10 nm to about 1000 nm, preferably of about 50 mn to about 400 nm.

For the production of liquid dispersions, a pre-emulsion is pumped through the aforementioned mixing device (dispersing unit). The pre-emulsion is at temperatures of about 20° C. to about 250° C., preferably of about 20° C. to about 200° C., and pressures of about 50 bar to about 2500 bar, preferably of about 100 bar to about 800 bar.

The residence time of the liquids to be mixed or to be dispersed in the mixing device is about $10^{-6}$ sec to about $10^{-1}$ sec.

As used herein, the term "pre-emulsion" denotes one of the following systems:

a) oil-in-water emulsion (O/W emulsion);

b) water-in-oil emulsion (W/O emulsion);

c) oil-in-water emulsion in which a lipophilic active substance is dissolved in the oil; and d) water immiscible solvent-in-water emulsion in which a lipophilic active substance is dissolved in this solvent.

An oil-in-water emulsion in which the viscosity of the dispersed phase is about 0.01 mPas to about 10,000 mPas, preferably about 0.1 mPas to about 2000 mPas, is preferred.

As used herein, the term "lipophilic active substance" includes vitamins A, D, E and K, carotenoids, and food additives, such as PUFAs (polyunsaturated fatty acids) and tocotrienols.

In the production of the pre-emulsion, the liquid to be dispersed is preferably stirred into an aqueous emulsifier solution, optionally while warming.

The processes for the production of finely divided liquid dispersions set forth herein relate not only to processes used in the food manufacturing field in which food emulsifiers are used, but also in general industrial dispersion processes in which corresponding industrial emulsifiers are used. Processes which are used in the food manufacturing field are preferred.

In the present invention, suitable emulsifiers/stabilizers for dispersions which may be added to foods include, for example, ascorbyl palmitate, lecithins, polysorbates, sugar esters, fatty acid esters, citric acid esters, sorbitol stearates; as well as colloids, for example gelatines and fish gelatines; carbohydrates, for example starches and starch derivatives such as dextrin, pectin or gum arabic; milk proteins and plant proteins. Mixtures of the aforementioned substances can also be used. Ascorbyl palmitate, fish gelatines or starch derivatives are preferred, with ascorbyl palmitate being especially preferred.

Suitable industrial emulsifiers are, for example, lauryl ethylene oxide (LEO)-9 and (LEO)-10.

The process in accordance with the invention is especially suitable for the production of liquid dispersions from oils, such as, for example, corn oil, palm oil, sunflower oil, and the like. The present process may also be used to produce liquid dispersions from lipophilic active substances, such as, for example, from vitamin A, D, E, and K, from carotenoids or from food additives such as PUFAs and tocotrienols.

In the present invention, suitable carotenoids include, for example, beta-carotene, beta-apo-4'-carotenal, beta-apo-8'-carotenal, beta-apo-12'-carotenal, beta-apo-8'-carotenoic acid, astaxanthin, canthaxanthin, zeaxanthin, cryptoxanthin, citranaxanthin, lutein, lycopene, torularodin aldehyde, torularodin ethyl ester, neurosporaxanthin ethyl ester, zetacarotene, dehydroplectania-xanthin and the like.

The aforementioned lipophilic active substances may be used directly insofar as they are oily substances. Solid active substances, for example carotenoids, may also be used in dissolved form in oil or in water-immiscible solvents.

Suitable water-immiscible solvents that may be used in the present invention include halogenated aliphatic hydrocarbons, such as for example, methylene chloride, water-immiscible esters, such as carboxylic acid dimethyl ester (dimethyl carbonate), ethyl formate, methyl, ethyl or isopropyl acetate; or water-immiscible ethers such as for example, methyl tert.butyl ether, and the like.

The process in accordance with the invention provides a very efficient mixing or dispersing process for liquids. The mixing or dispersing process in accordance with the invention is also suitable for performing chemical reactions having very short reaction times, for example on the order of seconds or fractions of seconds.

The mixing device in accordance with the invention has, in contrast to the known devices described above, an arrangement of the bores of the inlet and outlet nozzles which is axially spaced apart relative to one another. Thus, by the turbulence chamber being positioned between the nozzles, the short term stability of mixtures, especially of dispersions, is increased. This results in a liquid dispersion that is homogenized more strongly.

In FIG. 1, a supply container (1) is followed by a high pressure pump (2) which is optionally connected to a heat exchanger (3). The mixing device (4) is positioned thereafter.

Figure 2:
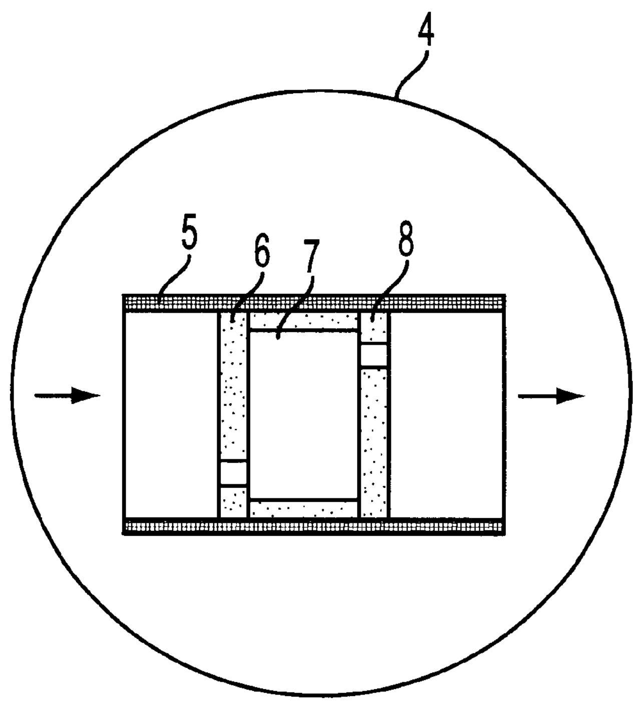
FIG. 2 shows a cross section through a mixing device in accordance with the invention having an inlet nozzle and an outlet nozzle.
Figure 3:
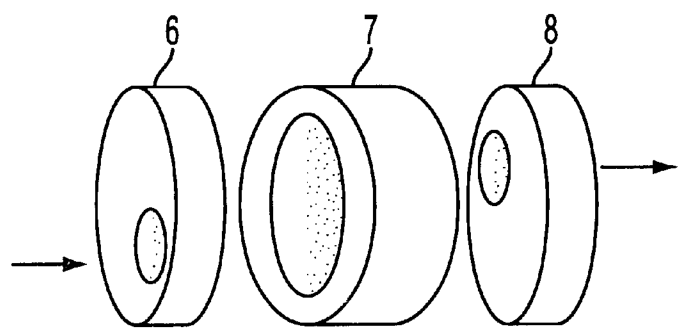
FIG. 3 shows a perspective view of the mixing device in accordance with the invention.

FIG. 2 and FIG. 3 show a mixing device (4) consisting of an inlet nozzle (6) having a bore diameter of about 0.05 mm to about 1 mm, preferably about 0.05 mm to about 0.5 mm; a turbulence chamber (7) having a diameter of about 0.5 mm to about 10 mm, preferably about 1 mm to about 10 mm, such as about 1 mm to about 5 mm; an outlet nozzle (8) having a bore diameter of about 0.05 mm to about 1.5 mm, preferably about 0.05 mm to about 0.8 mm, with the inlet nozzle (6), the turbulence chamber (7) and the outlet nozzle (8) being pressed in sequence in a cylindrical support (5). The inlet nozzle is in fluid communication with the outlet nozzle via the turbulence chamber. The bores of the nozzles are axially spaced apart relative to one another.

As used herein, the phrase "fluid communication" is intended to mean that liquids to be mixed or dispersed enter the turbulence chamber through the bore of the inlet nozzle. Once in the turbulence chamber, the liquids are mixed and then exit the chamber via the bore of the outlet nozzle.

In the present invention, the bores of the nozzles are said to be axially spaced apart relative to one another. Thus, as FIG. 2 indicates, the bores of the inlet and outlet nozzles are positioned on opposite sides of the axis of the chamber.

The ratio of length to diameter of each nozzle bore amounts in the case of the inlet nozzle or the outlet nozzle to about 1 to 10, preferably about 1 to 5.

The ratio of length to diameter of the turbulence chamber is about 0.5 to about 50, preferably about 0.5 to about 20, such as about 0.5 to about 10.

The diameter of the turbulence chamber must be greater than the diameter of the outlet nozzle.

The bore diameters of the inlet nozzle and the outlet nozzle may be the same or different. However, an embodiment in which the bore diameter of the inlet nozzle is smaller than the bore diameter of the outlet nozzle is preferred. For example, the bore diameter of the inlet nozzle is about 0.2 mm and the bore diameter of the outlet nozzle is about 0.25 mm.

The nozzles are suitably manufactured from wear-resistant materials such as e.g. sapphire, diamond, stainless steel, ceramic, silicon carbide, tungsten carbide, zirconium, and the like.

The bores of the nozzles may be round, rectangular, or elliptical. A bore which has a cone in the mouth is also suitable.

The cylindrical support (5) likewise consists of wear-resistant materials, suitably of stainless steel.

Figure 4A:
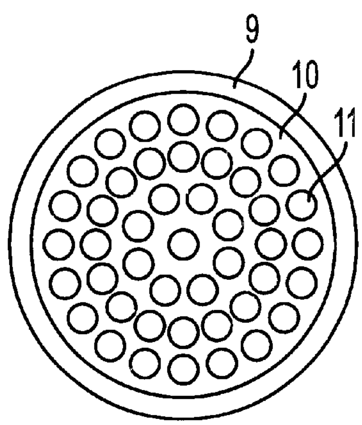
FIG. 4(*a–c*) shows a scale up arrangement.
Figure 4B:
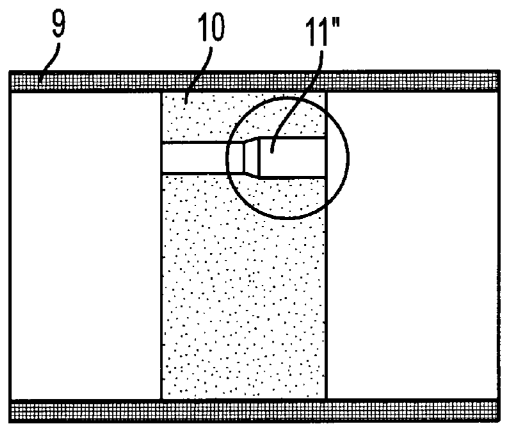
Figure 4C:
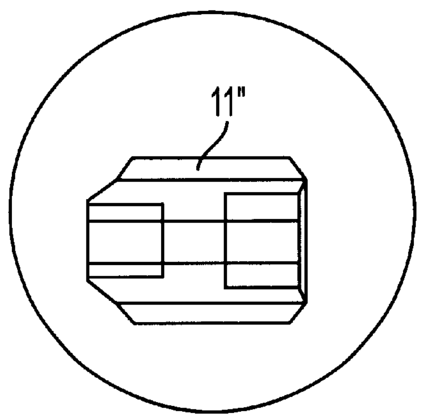

FIG. 4 shows one possibility for the scale up of the mixing device.

Section 4*a* shows a plurality of nozzles in accordance with the invention with nozzle inserts (11), which are secured to a support plate (10). In the present invention, the nozzle inserts may be secured to the support plate by any conventional means, such as for example, they may be screwed into the support plate. The support plate is positioned in a conduit (9) (cylindrical support).

Cross section 4*b* shows only one nozzle insert (11'). The nozzle insert (11'), the support plate (10) as well as the conduit (9) are manufactured from wear-resistant materials, preferably stainless steel.

Section 4c shows the screwable nozzle support (11") which contains the nozzle (4c) in accordance with the invention.

Figure 5:
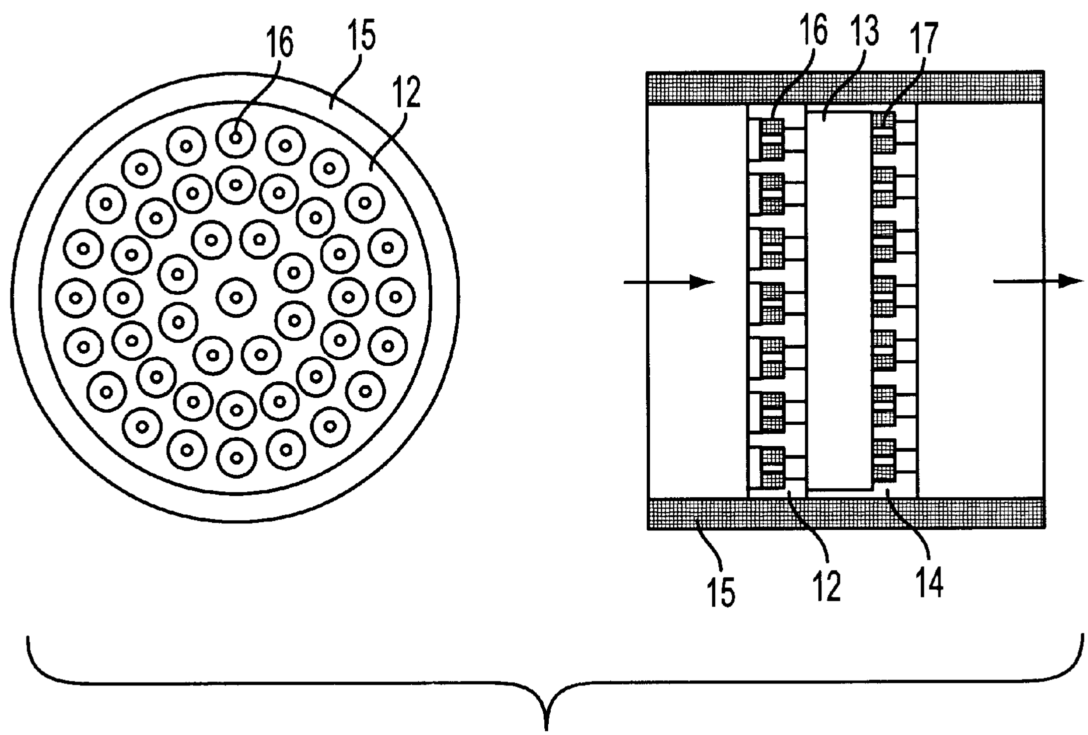
FIG. 5 shows another a scale up arrangement.

FIG. 5 shows another scale up arrangement. In this arrangement, the mixing device consisting of a support disk (12), a turbulence chamber (13) and a support disk (14), which are positioned in sequence in a tubular conduit (15), with the first support disk (12) containing a plurality of inlet nozzles (16) having a bore diameter of about 0.05 mm to about 1 mm, preferably about 0.05 mm to about 0.5 mm, and the second support disk (14) containing a plurality of outlet nozzles (17) having a bore diameter of about 0.05 mm to about 1 mm, preferably about 0.05 mm to about 0.8 mm. The bores of the inlet nozzles are in fluid communication with the bores of the outlet nozzles through the turbulence chamber and the bores of the inlet nozzles and outlet nozzles are axially spaced apart relative to one another.

The number of nozzles determines the diameter of the turbulence chamber (13). The ratio of length to diameter of the turbulence chamber is designed such that the residence time of a liquid to be dispersed in the dispersing unit is about $10^{-6}$ sec to about $10^{-1}$ sec.

As set forth in FIG. 1, for the production of a finely divided liquid dispersion, a pre-emulsion is first produced in the supply container (1) in a known manner and pumped through the dispersing unit (4) at temperatures of about 20° C. to about 250° C., preferably about 20° C. to about 200° C., and pressures of about 50 bar to about 2500 bar, preferably about 50 bar to about 800 bar, using a high pressure pump (2). Where required, the pre-emulsion may be heated for a brief period in the heat exchanger (3). The residence time of the liquid to be dispersed in the dispersing unit (4) is about $10^{-6}$ sec to about $10^{-1}$ sec.

The following examples are provided to further illustrate the present process. These examples are illustrative only and are not intended to limit the scope of the invention in any way.

In the Examples, in addition to the food emulsifier ascorbyl palmitate, industrial emulsifiers lauryl ethylene oxide (LEO)-9 and (LEO)-10 were also used. This is a so-called "more rapid" emulsifier which very rapidly stabilizes newly formed phase boundaries.

EXAMPLE 1

Corn Oil and Lauryl Ethylene Oxide

The emulsion had the following composition:

87 wt. % deionized water, 10 wt. % corn oil, and 3 wt. % lauryl ethylene oxide-9.

Deionized water was placed in a kettle and warmed to 40° C. The emulsifier lauryl ethylene oxide (LEO)-9 was dissolved in the water. Subsequently, the corn oil was stirred in and comminuted with an ULTRA TURRAX mixer at 1000 rpm. When the content of dispersed phase was 10 wt. %, the weight ratio of corn oil to lauryl ethylene oxide was 10:3. The pre-emulsion was homogenized three times at a pressure of 600 bar using the dispersing unit set forth in FIG. 2 in accordance with the invention. The geometric dimensions of the dispersing units used are set forth in Table 1. The particle sizes were determined in a known manner by means of photon correlation spectroscopy.

EXAMPLE 2

Corn Oil and Ascorbyl Palmitate

Here, ascorbyl palmitate was used as the emulsifier. The quantitative composition of the emulsion corresponded to that in Example 1.

Deionized water was placed in a kettle and warmed to 40° C. Ascorbyl palmitate was dissolved in the water at pH values between seven and eight. The production of the pre-emulsion and the homogenization were carried out according to Example 1.

EXAMPLE 3 dl-alpha-Tocopherol and Ascorbyl Palmitate dl-alpha-Tocopherol and ascorbyl palmitate were combined in accordance with Example 2.

EXAMPLE 4 dl-alpha-Tocopherol and Ascorbyl Palmitate

A pre-emulsion was produced in accordance with Example 2. The content of the dispersed phase was 30 wt. %. The weight ratio of dl-alpha-tocopherol to ascorbyl palmitate was 10:1. The pre-emulsion was homogenized once at pressures of 100 bar, 200 bar, 300 bar, 400 bar and 500 bar using the dispersing unit in accordance with the invention shown in FIG. 2.

EXAMPLE 5 dl-alpha-Tocopherol, Corn Oil with Ascorbyl Palmitate and Fish Gelatine

An emulsion containing 65 wt. % deionized water, 6 wt. % ascorbyl palmitate, 4 wt. % fish gelatine, 18 wt. % dl-alpha-tocopherol and 7 wt. % corn oil was produced in the manner described hereinafter.

The deionized water was placed in a kettle and warmed to 60° C. The fish gelatine was dissolved in the water. Then, the ascorbyl palmitate was dissolved in the aforementioned solution at pH values between seven and eight. Subsequently, the dispersed phase including dl-alpha-tocopherol and corn oil was stirred in as described in Example 1. The pre-emulsion was homogenized in accordance with Example 4.

Examples 6–10 are comparative Examples using a single-hole nozzle.

EXAMPLE 6

Corn Oil and Lauryl Ethylene Oxide

The pre-emulsion was produced in accordance with Example 1 and homogenized three times at a pressure of 600 bar in a single-hole nozzle. The single-hole nozzle had an acute angled inlet and outlet. The geometric dimensions of the single-hole nozzle are given in Table 1.

EXAMPLE 7

Corn Oil and Ascorbyl Palmitate

The pre-emulsion was produced in accordance with Example 2 and homogenized in the manner described in Example 6.

EXAMPLE 8 dl-alpha-Tocopherol and Ascorbyl Palmitate

The pre-emulsion was produced in accordance with Example 3 and homogenized in the manner described in Example 6.

EXAMPLE 9 dl-apha-Tocopherol and Ascorbyl Palmitate

The pre-emulsion was produced in accordance with Example 4 and homogenized once in a single-hole nozzle as described in Example 6 at pressures of 100 bar, 200 bar, 300 bar, 400 bar and 500 bar. The particle size was determined in a known manner by means of laser diffraction spectrometry and photon correlation spectroscopy.

EXAMPLE 10 dl-alpha-Tocopherol, Corn Oil with Ascorbyl Palmitate and Fish Gelatine

The pre-emulsion was produced in accordance with Example 5 and homogenized once in a single-hole nozzle as described in Example 6 at pressures of 100 bar, 200 bar, 300 bar, 400 bar and 500 bar.

TABLE 1

Geometric dimensions of the dispersing units used.

| Nozzle type | Bore diameter of the inlet nozzle [mm] | Bore diameter of the turbulence chamber [mm] | Length of the turbulence chamber [mm] | Bore diameter of the outlet nozzle [mm] |
|---|---|---|---|---|
| Nozzle I | 0.2 | 2 | 1.5 | 0.25 |
| Nozzle I long | 0.2 | 2 | 3 | 0.28 |
| Nozzle II | 0.2 | 2 | 1.5 | 0.2 |
| Single-hole nozzle | 0.2 | — | — | — |

The average particle sizes of the finely divided liquid dispersions of Examples 1–6 are set forth in Tables 2 and 3.

TABLE 2

Average particle sizes in nm of experiments 1, 2, 3, 6, 7 and 8.

| Example | Nozzle type | Passage 1 Particle size | Passage 2 Particle size | Passage 3 Particle size |
|---|---|---|---|---|
| 1 | Nozzle I 0.2/0.25 mm | 218<br>219 | 202<br>215 | 202<br>200 |
| 1 | Nozzle II 0.2/0.2 mm | 230<br>231 | 214<br>220 | 212<br>208 |
| 6 | single-hole nozzle 0.2 mm | 307<br>298 | 256<br>250 | 247<br>248 |
| 2 | Nozzle I 0.2/0.25 mm | 275 | 250 | 238 |
| 2 | Nozzle II 0.2/0.2 mm | 294 | 266 | 245 |
| 7 | single-hole nozzle 0.2 mm | 340 | 320 | 275 |
| 3 | Nozzle I 0.2/0.25 mm | 295 | 287 | 267 |
| 3 | Nozzle II 0.2/0.2 mm | 312 | 294 | 302 |
| 8 | single-hole nozzle 0.2 mm | 442 | 416 | 403 |

From Table I it is evident that the homogenization using nozzles I and II in accordance with the invention produces a liquid dispersion with a smaller particle size compared with the homogenization using a single-hole nozzle. When nozzles I and II are used, particle sizes up to a third smaller are produced compared with the single-hole nozzle.

The best homogenization takes place in nozzle I. Here, the particle size was reduced to 200 nm after a triple homogenization. The values from Example 1 reveal that the reproducibility of the results is also good.

The average particle sizes of the finely divided liquid dispersions obtained in Examples 4, 5, 9, and 10 are set forth in Table 3.

TABLE 3

Average particle sizes in nm of experiments 4, 5, 9 and 10.

| Ex. | Nozzle type | 100 bar Particle size [nm] | 200 bar Particle size [nm] | 300 bar Particle size [nm] | 400 bar Particle size [nm] | 500 bar Particle size [nm] |
|---|---|---|---|---|---|---|
| 4 | Nozzle I 0.2/0.25 mm | 1800 | 1370 | 1400 | 1105 | 1080 |
| 4 | Nozzle I/long 0.2/0.28 mm | 1370 | 740 | 745 | 660 | 600 |
| 9 | Single-hole nozzle 0.2 mm | 5200 | 3080 | 1520 | 1370 | 914 |
| 5 | Nozzle I 0.2/0.25 mm | 435 | 410 | 340 | 350 | 345 |
| 5 | Nozzle I/long 0.2/0.28 mm | 420 | 410 | 360 | 325 | 290 |
| 10 | Single-hole nozzle 0.2 mm | 440 | 430 | 360 | 350 | 355 |

From Table 3 it is evident that the homogenization using nozzle I and nozzle I/long liquid dispersions with a smaller particle size than the homogenization using a single-hole nozzle. The best homogenization takes place using nozzle I/long.

The invention being thus described, it will be obvious that the same may be varied in many ways. Such variations are not to be regarded as a departure from the spirit and scope of the invention, and all such modifications are intended to be included within the scope of the following claims.

We claim:

1. A process for mixing or dispersing liquids to produce a liquid dispersion having an average particle size of about 10 nm to about 1000 nm comprising:

(a) pumping at a pressure of about 50 bar to about 2500 bar a pre-emulsion of the liquids to be mixed or dispersed through the bore of the inlet nozzle of a mixing device, said mixing device having a cylindrical support comprising said inlet nozzle having a bore which is in fluid communication through a turbulence chamber with a bore of an outlet nozzle, wherein the bores of the nozzles are round, rectangular or elliptical and wherein the bores of the inlet and outlet nozzles are axially spaced apart relative to one another, wherein the length to diameter ratio of the inlet and outlet nozzle bores is about 1 to about 10, the bore diameter of the inlet nozzle is about 0.05 mm to about 1 mm, the diameter of the turbulence chamber is about 0.5 mm to about 10 mm, the bore diameter of the outlet nozzle is about 0.05 mm to about 1.5 mm, the bore diameter of the inlet nozzle is smaller than the bore diameter of the outlet nozzle, and wherein the inlet and outlet nozzles are manufactured from a material selected from the group consisting of sapphire, diamond, stainless steel, ceramic, silicon carbide, tungsten carbide, and zirconium oxide; and (b) allowing a residence time of the liquids to be mixed or dispersed in the mixing device of about $10^{-6}$ sec to about $10^{-1}$ sec.

2. A process according to claim 1 further comprising heating the liquids to be mixed or dispersed to a temperature of about 20° C. to about 250° C. prior to distributing the liquids through the mixing device.

3. A process according to claim 2 further comprising heating the liquids to be mixed or dispersed to a temperature of about 20° C. to about 200° C. at a pressure of about 100 bar to about 800 bar.

4. A process according to claim 1 wherein a liquid dispersion having an average particle size of about 10 nm to about 1000 nm is produced.

5. A process according to claim 1 wherein a liquid dispersion having an average particle size of about 50 nm to about 400 nm is produced.

6. A process according to claim 1 wherein the pre-emulsion is an oil-in-water emulsion wherein a viscosity of a dispersed phase of the emulsion is about 0.01 mPas to about 10,000 mPas.

7. A process according to claim 6 wherein the viscosity of the dispersed phase of the emulsion is about 0.1 mPas to about 2,000 mPas.

8. A process according to claim 1 wherein the pre-emulsion is produced by stirring the liquid to be dispersed into an aqueous emulsifier solution.

9. A process according to claim 8 wherein the emulsifier is ascorbyl palmitate.

10. A process according to claim 1 wherein the pre-emulsion is produced by stirring the liquid to be dispersed into an aqueous emulsifier solution while warming.

11. A process according to claim 1 wherein the liquid to be dispersed is an oil or a lipophilic active substance.

12. A process according to claim 1 wherein a lipophilic active substance is mixed or dispersed into a liquid in the mixing device.

13. A process according to claim 12 wherein the lipophilic active substance is selected from the group consisting of vitamin A, vitamin D, vitamin E, vitamin K, carotenoids, food additives, and mixtures thereof.

14. A process according to claim 13 wherein the food additive is selected from the group consisting of polyunsaturated fatty acids, tocotrienols, and mixtures thereof.

* * * * *